United States Patent
Zakataeva et al.

(10) Patent No.: US 9,012,182 B2
(45) Date of Patent: Apr. 21, 2015

(54) **METHOD FOR PRODUCING PURINE NUCLEOSIDES AND NUCLEOTIDES BY FERMENTATION USING BACTERIUM BELONGING TO THE GENUS *BACILLUS* OR *ESCHERICHIA***

(75) Inventors: Natalia Pavlovna Zakataeva, Moscow (RU); Vitaly Arkadievich Livshits, Moscow (RU); Sergey Viktorovich Gronsky, Moscow (RU); Ekaterina Aleksandrovna Kutukova, Moscow (RU); Anna Evgenievna Novikova, Moscow (RU); Yury Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 1876 days.

(21) Appl. No.: 11/536,863

(22) Filed: Sep. 29, 2006

(65) Prior Publication Data

US 2008/0241888 A1  Oct. 2, 2008

Related U.S. Application Data

(63) Continuation of application No. PCT/JP2005/006833, filed on Mar. 31, 2005.

(30) Foreign Application Priority Data

Mar. 31, 2004 (RU) ............................... 2004109599
Feb. 22, 2005 (RU) ............................... 2005104627

(51) Int. Cl.
| | | |
|---|---|---|
| *C12P 19/38* | (2006.01) | |
| *C12P 19/30* | (2006.01) | |
| *C12P 19/32* | (2006.01) | |
| *C12N 1/20* | (2006.01) | |
| *C12P 19/40* | (2006.01) | |
| *C07K 14/245* | (2006.01) | |
| *C07K 14/32* | (2006.01) | |

(52) U.S. Cl.
CPC .............. *C12P 19/40* (2013.01); *C07K 14/245* (2013.01); *C07K 14/32* (2013.01)

(58) Field of Classification Search
None
See application file for complete search history.

(56) References Cited

U.S. PATENT DOCUMENTS

| | | | |
|---|---|---|---|
| 3,258,408 A * | 6/1966 | Okumura et al. ............. | 435/88 |
| 3,736,228 A | 5/1973 | Nakayama et al. | |
| 3,912,587 A | 10/1975 | Enei et al. | |
| 3,960,660 A | 6/1976 | Enei et al. | |
| 3,960,661 A | 6/1976 | Enei et al. | |
| 4,701,413 A | 10/1987 | Miyagawa et al. | |
| 4,749,650 A * | 6/1988 | Kenichiro et al. ............. | 435/88 |
| 6,010,851 A | 1/2000 | Mihara et al. | |
| 6,015,697 A | 1/2000 | Mihara et al. | |
| 6,207,435 B1 | 3/2001 | Mihara et al. | |
| 6,284,495 B1 | 9/2001 | Sato et al. | |
| 6,355,472 B2 | 3/2002 | Mihara et al. | |
| 6,673,576 B1 | 1/2004 | Usuda et al. | |
| 6,887,691 B2 | 5/2005 | Livshits et al. | |
| 6,960,455 B2 | 11/2005 | Livshits et al. | |
| 6,979,560 B1 | 12/2005 | Livshits et al. | |
| 6,987,008 B1 | 1/2006 | Ishikawa et al. | |
| 2002/0058314 A1 | 5/2002 | Livshits et al. | |
| 2002/0098494 A1 | 7/2002 | Kakehi et al. | |
| 2002/0098552 A1 | 7/2002 | Livshits et al. | |
| 2003/0148473 A1 | 8/2003 | Livshits et al. | |
| 2004/0038380 A1 | 2/2004 | Debabov et al. | |
| 2004/0132165 A1 | 7/2004 | Akhverdian et al. | |
| 2004/0166575 A1 | 8/2004 | Tominaga et al. | |
| 2004/0229320 A1 | 11/2004 | Stoynova et al. | |
| 2004/0229321 A1 | 11/2004 | Savrasova et al. | |
| 2005/0048631 A1 | 3/2005 | Klyachko et al. | |
| 2005/0054061 A1 | 3/2005 | Klyachko et al. | |
| 2005/0124048 A1 | 6/2005 | Akhverdian et al. | |
| 2005/0176033 A1 | 8/2005 | Klyachko et al. | |
| 2005/0202543 A1 | 9/2005 | Livshits et al. | |
| 2005/0214911 A1 | 9/2005 | Marchenko et al. | |
| 2005/0214913 A1 | 9/2005 | Marchenko et al. | |
| 2005/0239177 A1 | 10/2005 | Livshits et al. | |
| 2006/0014258 A1 | 1/2006 | Livshits et al. | |
| 2006/0030009 A1 | 2/2006 | Livshits et al. | |
| 2006/0035346 A1 | 2/2006 | Savrasova et al. | |
| 2006/0040364 A1 | 2/2006 | Livshits et al. | |
| 2006/0040365 A1 | 2/2006 | Kozlov et al. | |
| 2006/0057685 A1 | 3/2006 | Stoynova et al. | |

(Continued)

FOREIGN PATENT DOCUMENTS

| | | |
|---|---|---|
| EP | 0273660 | 7/1988 |
| EP | 0286303 | 10/1988 |

(Continued)

OTHER PUBLICATIONS

Sauer et al. (Biotechnology and Bioengineering, vol. 59, No. 2, 1998, pp. 227-238).*
Machine translation of JP2003-259861, Sep. 2003, Livshits et al.*
Kuninaka, Nucleotide and related compounds, Chapter 15, Biotecnology Second Edition, 1996.*
Priest, *Bacillus*, Chapter 11, Biotechnology, 1993.*
Kunst et al., The complete genome sequence of the Gram-positive bacterium *Bacillus subtilis*, Nature, vol. 390, 1997.*
Smallwood et al., Different Substitutions at Conserved Amino Acids in Domains II and III in the Sendai L RNA Polymerase Protein Inactivate Viral RNA Synthesis, Virology 304, 135-145 (2002).*

(Continued)

*Primary Examiner* — Taeyoon Kim
*Assistant Examiner* — Srikanth Patury
(74) *Attorney, Agent, or Firm* — Shelly Guest Cermak; Cermak Nakajima & McGowan LLP

(57) ABSTRACT

Methods for producing purine nucleosides, and purine nucleotides, such as inosine and 5'-inosinic acid are provided which include using a bacterium belonging to the genus *Bacillus* or to the genus *Escherichia* wherein the purine nucleoside productivity of said bacterium is enhanced by increasing an activity of the YdhL protein. Also disclosed is the amino acid sequence of the YdhL protein from *Bacillus amyloliquefaciens* and the gene encoding it.

6 Claims, 2 Drawing Sheets

(56) References Cited

U.S. PATENT DOCUMENTS

2006/0088919 A1 4/2006 Rybak et al.
2006/0141586 A1 6/2006 Rybak et al.
2006/0160192 A1 7/2006 Rybak et al.

FOREIGN PATENT DOCUMENTS

| EP | 0393969 | | 10/1990 |
|---|---|---|---|
| EP | 0412688 | | 2/1991 |
| EP | 0465132 | | 1/1992 |
| GB | 1139097 | | 1/1969 |
| JP | 51-5075 | B | 2/1976 |
| JP | 51-125794 | | 11/1976 |
| JP | 54-17033 | B | 6/1979 |
| JP | 55-2956 | B | 1/1980 |
| JP | 55-114295 | | 9/1980 |
| JP | 55-45199 | B | 11/1980 |
| JP | 55-162990 | | 12/1980 |
| JP | 57-14160 | B | 3/1982 |
| JP | 57-41915 | B | 9/1982 |
| JP | 58-17592 | B | 4/1983 |
| JP | 58-158197 | | 9/1983 |
| JP | 58-175493 | | 10/1983 |
| JP | 59-028470 | | 2/1984 |
| JP | 59-42895 | | 3/1984 |
| JP | 60-156388 | | 8/1985 |
| JP | 64-27477 | | 1/1989 |
| JP | 1-174385 | | 7/1989 |
| JP | 3-58787 | | 3/1991 |
| JP | 3-164185 | | 7/1991 |
| JP | 05-084067 | | 4/1993 |
| JP | 5-192164 | | 8/1993 |
| JP | 06-113876 | | 4/1994 |
| JP | 2003-219876 | | 8/2003 |
| JP | 2003-259861 | * | 9/2003 |

OTHER PUBLICATIONS

International Preliminary Report on Patentability for PCT Patent App. No. PCT/JP2005/006833 (Oct. 12, 2006).
Pao, S. S., et al., "Major Facilitator Superfamily," Microbiol. Mol. Biol. Rev. 1998;62(1):1-34.
Paulsen, I. T., et al., "Microbial Genome Analyses: Global Comparisons of Transport Capabilities Based on Phylogenies, Bioenergetics and Substrate Specificities," J. Mol. Biol. 1998;277:573-592.
Saler, Jr., M. H., et al., "The Major Facilitator Superfamily," J. Mol. Microbiol. Biotechnol. 1999;1(2):257-279.
English Translation of Thai Patent App. No. 0301000190, pp. 1-62.
English Translation of Thai Patent App. No. 0301000416, pp. 1-35.
Johansen, L. E., et al., "Definition of a Second *Bacillus subtilis pur* Regulon Comprising the *pur* and *xpt-pbuX* Operons plus *pbuG, nupG (yxjA)*, and *pbuE (ydhL)*," J. Bacteriol. 2003;185(17):5200-5209.
Mandal, M., et al., "Adenine riboswitches and gene activation by disruption of a transcription terminator," Nature Struc. Mol. Biol. 2004;11(1):29-35.
Nygaard, P., et al., "The Purine Efflux Pump PhuE in *Bacillus subtilis* Modulates Expression of the PurR and G-Box (XptR) Regulons by Adjusting the Purine Base Pool Size," J. Bacteriol. 2005;187(2):791-794.
International Search Report for PCT Patent App. No. PCT/JP2005/006833 (Nov. 15, 2005).
Written Opinion of the International Searching Authority for PCT Patent App. No. PCT/JP2005/006833 (Nov. 15, 2005).
Office Communication from European Patent App. No. 05728770.8 (Jun. 10, 2009).

* cited by examiner

Fig. 1

```
YDHL_BS    MNFKVFLLAASTIAVGLVELIVGGILPQIANDLDISIVSAGQLISVFALGYAVSGPLLLA  60
YDHL_BA    MNFKVFLLAASTIAVGLVELIVGGILPQIASDLDISIVSAGQLISVFALGYAVSGPLLLA  60
           ****************************** *****************************

YDHL_BS    LTAKIERKRLYLIALFVFFLSNLVAYFSPNFATLMVSRVLAAMSTGLIVVLSLTIAPKIV  120
YDHL_BA    VTAKAERKRLYLIALFVFFLSNLVAYFSPNFAVLMVSRVLASMSTGLIVVLSLTIAPKIV  120
           :*** ***************************:*******:*******************

YDHL_BS    APEYRARAIGIIFMGFSSAIALGVPLGILISDSFGWRILFLGIGLLALISMLIISIFFER  180
YDHL_BA    APEYRARAIGIIFMGFSSAIALGVPVGIIISNAFGWRVLFLGIGVLSLVSMLIISVFFEK  180
           *************************.**:**:****:******:*:*.******:***:

YDHL_BS    IPAEKMIPFREQLKTIGNLKIASSHLVTMFTLAGHYTLYAYFAPFLEETLHLSSFWVSIC  240
YDHL_BA    IPAEKMIPFREQIKTIGNAKIASAHLVTLFTLAGHYTLYAYFAPFLETTLHLSSVWVSVC  240
           ************:*****.****:****:****************** ******.***:*

YDHL_BS    YFLFGISAVCGGPFGGALSDRLGSFKSILLVTGSFAIIMFLLPLSTSSMIFFLPVMVIWG  300
YDHL_BA    YFLFGLSAVCGGPFGGWLYDRLGSFKSIMLVTVSFALILFILPLSTVSLIVFLPAMVIWG  300
           *****:********** * *********:***.***:::*:*****.*:*:***.*****

YDHL_BS    LLSWSLAPAQQSYLIEIAPDSSDIQQSFNTSALQVGIALGSAIGGVVLDQTGTVVSTAWC  360
YDHL_BA    LLSWSLAPAQQSYLIKIAPESSDIQQSFNTSALQIGIALGSAIGGVIGQTGSVTATAWC  360
           ***************.***:************** **********: ***.*.:*:****

YDHL_BS    GGSIVIIAVLFAFISLTRPVQTAKKSSL  388
YDHL_BA    GGLIVIIAVSLAVFSLTRPALKRKSA--  386
           ** ******  :*::*****: : *:::
```

METHOD FOR PRODUCING PURINE NUCLEOSIDES AND NUCLEOTIDES BY FERMENTATION USING BACTERIUM BELONGING TO THE GENUS BACILLUS OR ESCHERICHIA

This application is a continuation under 35 U.S.C. §120 of PCT/JP2005/006833, filed Mar. 31, 2005, and claims priority under 35 U.S.C. §119 to Russian Patent Application No. 2004109599, filed Mar. 31, 2004, and Russian Patent Application No. 2005104627, filed Feb. 22, 2005, all of which are incorporated by reference. The Sequence Listing on Compact Disk filed herewith is also hereby incorporated by reference in its entirety (File Name: US-166 Seq List; File Size: 20 KB; Date Created Sep. 29, 2006).

FIELD OF THE INVENTION

The present invention relates to a method for producing purine nucleosides, which are important as a raw material in the syntheses of 5'-inosinic acid and 5'-guanylic acid. The present invention also relates to novel microorganisms used in the production method. The present invention also relates to novel DNA and protein species which confer to a bacterium expressing the novel DNA resistance to purine base analogues and purine nucleosides.

BRIEF DESCRIPTION OF THE RELATED ART

Conventionally, nucleosides such as inosine have been industrially produced via fermentation methods which utilize adenine auxotrophic strains or strains which have been imparted with drug resistance to various drugs, such as purine analogues and sulfaguanidine. Examples of such strains include strains belonging to the genus Bacillus (Japanese Patent Publication 54-17033 (1979), 55-2956 (1980), and 55-45199 (1980), Japanese Patent Application Laid-Open No. 56-162998 (1981), Japanese Patent Publication Nos. 57-14160 (1982) and 57-41915 (1982), and Japanese Patent Application Laid-Open No. 59-42895 (1984)), or the genus Brevibacterium (Japanese Patent Publication Nos. 51-5075 (1976) and 58-17592 (1972), and Agric. Biol. Chem., 42, 399 (1978)), or the genus Escherichia (WO9903988) and the like.

Acquisition of such mutant strains typically involves subjecting microorganisms to a mutagenesis treatment such as UV irradiation or nitrosoguanidine (N-methyl-N'-nitro-N-nitrosoguanidine) treatment, and selecting the desired strain via a suitable selection medium. On the other hand, the breeding of such mutant strains using genetic engineering techniques has also been practiced for strains belonging to the genus Bacillus (Japanese Patent Application Laid-Open Nos. 58-158197 (1983), 58-175493 (1983), 59-28470 (1984), 60-156388 (1985), 1-27477 (1989), 1-174385 (1989), 3-58787 (1991), 3-164185 (1991), 5-84067 (1993), and 5-192164 (1993)), or the genus Brevibacterium (Japanese Patent Application Laid-Open No. 63-248394 (1988)), or the genus Escherichia (WO9903988).

The productivity of these inosine-producing strains could be further improved by increasing the inosine-secretion ability. Currently, it is generally accepted that the penetration of metabolites across the cytoplasmic cell membrane is usually mediated by specific efflux transporter proteins (Pao, S. S. et al., Microbiol. Mol. Biol. Rev., 62 (1), 1-34, (1998); Paulsen, I. T. et al., J. Mol. Biol., 277, 573-592 (1998); Saier, M. H. et al., J. Mol. Microbiol. Biotechnol., 257-279 (1999)). The present inventors have previously shown that inosine- or xanthosine-producing strains belonging to the genus Escherichia or Bacillus which have an enhanced activity of the RhtA protein encoded by the rhtA (ybif) gene, an enhanced activity of the YijE protein encoded by the yijE gene, and an enhanced activity of the YdeD protein encoded by the ydeD gene produced more inosine or xanthosine than their respective parental strains (Japanese Patent Application Laid-Open No. 2003-219876A, Russian patent Nos. 2244003C and 2244004C, respectively). Recently, YdhL from B. subtilis was found to lower the sensitivity to the purine analogue 2-fluoroadenine. Besides, indirect evidence indicates that YdhL decreases the amount of the internal pool of hypoxanthine (Johansen et al, J. Bacteriol., 185, 5200-5209, 2003). However, the effect of YdhL overexpression on nucleoside secretion and/or nucleoside production has not been shown.

Moreover, YdhL from Bacillus amyloliquefaciens has never been reported, nor has the effect of YdhL overexpression on nucleoside secretion and/or nucleoside production ever been shown.

SUMMARY OF THE INVENTION

An object of the present invention is to enhance production of purine nucleosides by purine nucleoside-producing strains as well as provide methods for producing inosine and 5'-inosinic acid using these strains.

This object was achieved by identifying the ydhL gene of B. subtilis. This gene encodes a putative membrane protein which confers resistance to purine base analogues, such as 8-azaadenine, 6-methylpurine, 2,6-diaminopurine, 6-mercaptopurine, 8-azaguanine and purine nucleosides, such as inosine and guanosine, when the wild-type allele of the gene placed on a multicopy vector was introduced into an E. coli strain. Also, the previously unknown ydhL gene from Bacillus amyloliquefaciens was isolated and its nucleotide sequence was determined. Furthermore, it was determined that the ydhL gene from Bacillus subtilis or Bacillus amyloliquefaciens can enhance purine nucleoside production when additional copies of the gene are introduced into the cells of the respective inosine-producing strain belonging to the genus Bacillus or genus Escherichia. Thus the present invention has been completed.

Thus, the present invention provides a microorganism belonging to the genus Bacillus or genus Escherichia which has an ability to produce purine nucleosides.

It is an object of the present invention to provide YdhL protein from Bacillus amyloliquefaciens selected from the group consisting of:
(A) a protein which comprises the amino acid sequence shown in SEQ ID NO: 2; and
(B) a protein which comprises an amino acid sequence of SEQ ID NO: 2, and which includes a deletion, substitution, insertion or addition of one or several amino acids, and which has an activity of making a bacterium belonging to the genus Bacillus or to the genus Escherichia resistant to purine base analogues and/or purine nucleosides such as inosine, and guanosine, when said activity of said protein is enhanced in said bacterium.

It is a further object of the present invention to provide a DNA coding for the protein described above.

It is a further object of the present invention to provide the DNA as described above, wherein said DNA is selected from the group consisting of:
(a) a DNA which comprises the nucleotide sequence of SEQ ID No. 1, and
(b) a DNA which is hybridizable with the nucleotide sequence of SEQ ID NO: 1 under stringent conditions and encodes a protein having an activity of making a bacterium belonging to the genus *Bacillus* or to the genus *Escherichia* resistant to purine base analogues and/or purine nucleosides when activity of said protein is enhanced in said bacterium.

It is a further object of the present invention to provide the DNA as described above, wherein the stringent conditions comprise washing with 1×SSC, 0.1% SDS, at 60° C.

It is a further object of the present invention to provide a bacterium, which belongs to the genus *Bacillus* or to the genus *Escherichia*, wherein said bacterium has a purine nucleoside-producing ability, and said bacterium has enhanced activity of a YdhL protein.

It is a further object of the present invention to provide the bacterium as described above, wherein the activity of said YdhL protein has been enhanced by increasing a copy number of a ydhL gene, or by modifying an expression regulatory sequence of the ydhL gene.

It is a further object of the present invention to provide the bacterium as described above, wherein said ydhL gene is selected from the group consisting of:
(a) a DNA comprising a nucleotide sequence of SEQ ID NO: 1; and
(b) a DNA which is able to hybridize under stringent conditions with a nucleotide sequence of SEQ ID NO: 1 or a probe that can be prepared from the nucleotide sequence of SEQ ID NO: 1, and which encodes a protein having an activity of making a bacterium belonging to the genus *Bacillus* or to the genus *Escherichia* resistant to purine base analogues and/or purine nucleosides when activity of said protein is enhanced in said bacterium.

It is a further object of the present invention to provide the bacterium as described above, wherein the stringent conditions comprise washing with 1×SSC, 0.1% SDS, at 60° C.

It is a further object of the present invention to provide the bacterium as described above, wherein said ydhL gene is selected from the group consisting of:
(a) a DNA comprising a nucleotide sequence of SEQ ID NO: 3; and
(b) a DNA hybridizable under stringent conditions with a nucleotide sequence of SEQ ID NO: 3 or a probe that can be prepared from the nucleotide sequence of SEQ ID NO: 3, and which encodes a protein having an activity of making a bacterium belonging to the genus *Bacillus* or to the genus *Escherichia* resistant to purine base analogues and/or purine nucleosides when activity of said protein is enhanced in said bacterium.

It is a further object of the present invention to provide the bacterium as described above, wherein the stringent conditions comprise washing with 1×SSC, 0.1% SDS, at 60° C.

It is a further object of the present invention to provide a bacterium belonging to the genus *Bacillus* or to the genus *Escherichia* which bacterium has a purine nucleoside-producing ability, and said bacterium has an enhanced activity of a protein selected from the group consisting of
(A) a protein encoded by a ydhL gene from *Bacillus amyloliquefaciens*,
(B) a protein encoded by a ydhL gene from *Bacillus subtilis*, and
(C) a protein encoded by an ortholog of either of said ydhL genes in (A) or (B).

It is a further object of the present invention to provide the bacterium described above, wherein the purine nucleoside is inosine, xanthosine, or guanosine.

It is a further object of the present invention to provide the bacterium described above, wherein the activity of the protein is enhanced by transformation of the bacterium with a DNA coding for the protein, or by alteration of an expression regulatory sequence of said DNA on the chromosome of the bacterium.

It is a further object of the present invention to provide the bacterium described above, wherein the transformation is performed with a low copy number vector.

It is a further object of the present invention to provide a method for producing a purine nucleoside comprising cultivating the bacterium described above in a culture medium, allowing said purine nucleoside to be secreted into said culture medium, and collecting said purine nucleoside from the culture medium It is a further object of the present invention to provide the method described above, wherein the purine nucleoside is inosine, xanthosine, or guanosine.

It is a further object of the present invention to provide the method as described above, wherein the bacterium has been modified to have an enhanced expression of purine nucleoside biosynthesis genes.

It is a further object of the present invention to provide a method for producing purine nucleotides comprising cultivating the bacterium as described above in a culture medium, phosphorylating the purine nucleoside to generate purine nucleotides, allowing the purine nucleotide to be secreted into said culture medium, and collecting purine nucleotide.

It is a further object of the present invention to provide the method as described above, wherein the purine nucleotide is 5'-inosinic acid, 5'-xanthylic acid, or 5'-guanylic acid.

It is a further object of the present invention to provide the method described above, wherein the bacterium has been modified to have an enhanced expression of purine nucleoside biosynthesis genes.

It is a further object of the present invention to provide a method for producing 5'-guanylic acid comprising cultivating a bacterium as described above in a culture medium, phosphorylating xanthosine to generate 5'-xanthylic acid, aminating 5'-xanthylic acid to generate 5'-guanylic acid, and collecting 5'-guanylic acid.

The present invention is described in detail below.

BRIEF DESCRIPTION OF THE DRAWINGS

FIG. 1 shows an alignment of the *B. amyloliquefaciens* YdhL protein (YDHL_BA; SEQ ID NO: 2) coded by a DNA fragment within the pYDHL4 plasmid, and the *B. subtilis* YdhL protein (YDHL BS; SEQ ID NO: 3) coded by a DNA fragment within the pYDHL1 plasmid. The symbol "*" means a common amino acid between YDHL_BA and YDHL_BS. The symbol ":" means a similarity of amino acid between YDHL_BA and YDHL_BS.

DESCRIPTION OF THE PREFERRED EMBODIMENTS

Figure 2:
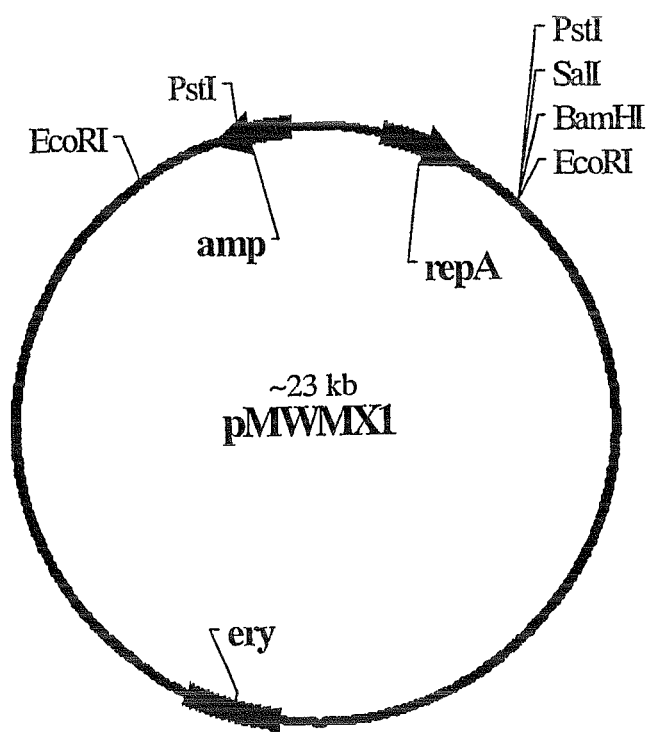
FIG. 2 shows the structure of the pMWMX1 plasmid.

I. The Proteins of the Present Invention

The proteins of the present invention encompass a protein which has the amino acid sequence shown in SEQ ID NO: 2 or 4, and a protein which has an amino acid sequence which includes deletions, substitutions, insertions or additions of one or several amino acids in the amino acid sequence shown in SEQ ID NO: 2 or 4, and which has an activity of making a bacterium belonging to the genus *Bacillus* or to the genus *Escherichia* resistant to purine base analogues, or purine nucleosides such as inosine or guanosine.

The protein which has the amino acid sequence shown in SEQ ID NO: 2 is YdhL protein from *Bacillus amyloliquefa-*

*ciens*. The amino acid sequence of the protein and nucleotide sequence of ydhL gene have not been previously disclosed.

The YdhL protein from *Bacillus subtilis* is not involved in the biosynthetic pathway of purine nucleotides and belongs to the Major Facilitator Superfamily (Pao, S. S., et al, Microbiol. Mol. Biol. Rev. 62 (1): 1-32, (1998)) and to the arabinose efflux permease cluster of the orthologous group (COG) 2814 (Tatusov, R. L. et al, Nucleic Acids Res., 29: 22-28 (2001)). *E. coli* proteins belonging to this family, AraJ and YdeA, are also involved in arabinose export (Bost, S. et al, J. Bacteriol., 181: 2185-2191 (1999)). The genome of *Bacillus subtilis* contains the following 5 genes which encode homologs of the ydhL gene: ybcL, yceJ, yfhI, ytbD, and ywfA. The YdhL protein from *B. subtilis* is a highly hydrophobic protein composed of 388 amino acids, and contains 12 putative transmembrane segments having unknown function. The YdhL protein is encoded by the ydhL gene. The ydhL gene of *Bacillus subtilis* subsp. *subtilis* strain 168 (numbers from 624675 to 625838 in GenBank, accession number CAB12399.2; GI:32468705) is located on chromosome between the ydhK and ydhM genes at 53.50°.

The number of "several" amino acids which can be altered in the proteins of the present invention differs depending on the position and/or the type of amino acid residue in the three dimensional structure of the protein. It may be 1 to 40, preferably 1 to 20, and more preferably 1 to 5 for the protein as shown in SEQ ID No. 2 or 4. This is due to the fact that some amino acids are highly homologous to one another, so the three dimensional structure or activity is not affected by such a change. Therefore, the protein which has an amino acid sequence which includes deletions, substitutions, insertions or additions of one or several amino acids in the amino acid sequence shown in SEQ ID NO: 2 or 4 may be one which has homology of not less than 30 to 50%, preferably 50 to 70%, and most preferably 70 to 90% with respect to the entire amino acid sequence of YdhL protein, and which also retains the activity of the protein.

A protein having a homology of not less than 90%, preferably not less than 95%, more preferably not less than 98%, to the amino acid sequence shown in SEQ ID No. 2 or 4 and which retains the activity of the YdhL protein is encompassed by the present invention and is the most preferred.

To evaluate the degree of homology, several well-known calculation methods, such as BLAST search, FASTA search, and CrustalW, can be used.

BLAST (Basic Local Alignment Search Tool) is the heuristic search algorithm employed by the programs blastp, blastn, blastx, megablast, tblastn, and tblastx; these programs assign significance to their findings using the statistical methods of Karlin, Samuel and Stephen F. Altschul ("Methods for assessing the statistical significance of molecular sequence features by using general scoring schemes". Proc. Natl. Acad. Sci. USA, 87:2264-68 (1990); "Applications and statistics for multiple high-scoring segments in molecular sequences". Proc. Natl. Acad. Sci. USA, 90:5873-7 (1993)). The FASTA search method is described by W. R. Pearson ("Rapid and Sensitive Sequence Comparison with FASTP and FASTA", Methods in Enzymology, 183:63-98 (1990)). The ClustalW method is described by Thompson J. D., Higgins D. G. and Gibson T. J. ("CLUSTAL W: improving the sensitivity of progressive multiple sequence alignment through sequence weighting, position-specific gap penalties and weight matrix choice", Nucleic Acids Res. 22:4673-4680 (1994)).

Changes to the proteins of the present invention such as those described above are typically conservative changes so as to maintain the activity of the protein. Substitution changes include those in which at least one residue in the amino acid sequence has been removed and a different residue is inserted in its place. Examples of amino acids which may be substituted for an original amino acid in the above protein and which are regarded as conservative substitutions include ala substituted with ser or thr; arg substituted with gln, his, or lys; asn substituted with glu, gln, lys, his, asp; asp substituted with asn, glu, or gln; cys substituted with ser or ala; gln substituted with asn, glu, lys, his, asp, or arg; glu substituted with asn, gln, lys, or asp; gly substituted with pro; his substituted with asn, lys, gln, arg, tyr; ile substituted with leu, met, val, phe; leu substituted with ile, met, val, phe; lys substituted with asn, glu, gln, his, arg; met substituted with ile, leu, val, phe; phe substituted with trp, tyr, met, ile, or leu; ser substituted with thr, ala; thr substituted with ser or ala; trp substituted with phe, tyr; tyr substituted with his, phe, or trp; and val substituted with met, ile, leu.

The "activity" in reference to the proteins of the present invention means one which makes a bacterium harboring the protein resistant to purine base analogues, such as 8-azaadenine, 2,6-diaminopurine, 6-mercaptopurine, 6-thioguanine, and/or resistant to purine nucleosides, such as inosine and guanosine.

The phrase "resistant to purine base analogues and/or purine nucleosides" means a characteristic of a bacterium to grow on minimal medium containing purine base analogues, such as 8-azaadenine, 6-methylpurine, 2,6-diaminopurine, 6-mercaptopurine, 8-azaguanine, or purine nucleosides such as inosine or guanosine, in concentration, whereby the wild-type or parental strain cannot grow under similar conditions, or a characteristic of a bacterium to grow on the medium containing the purine base analogues or purine nucleosides faster than the wild-type or parental strain of the bacterium. The above-mentioned concentration of the purine base analogues is 300 µg/ml for 8-azaadenine; 400 µg/ml for 2,6-diaminopurine; 400 µg/ml for 6-mercaptopurine; and for the purine base nucleosides, it is 300 µg/ml, preferably 1000 µg/ml, for inosine, and 10 µg/ml for guanosine.

II. The Bacterium of the Present Invention

The bacterium of the present invention is a bacterium wherein purine nucleoside production by the bacterium is enhanced by increasing an activity of the protein. More specifically, the bacterium of present invention is a bacterium wherein purine nucleoside production by the bacterium is enhanced by increasing an activity of the protein of the present invention in the bacterium. Even more specifically, the bacterium of the present invention harbors the DNA of the ydhL gene or its ortholog on the chromosome or a plasmid in the bacterium. The DNA of the ydhL gene or its ortholog is overexpressed, and as a result, the bacterium has an ability to produce greater amounts of purine nucleosides.

Enhancement of the ydhL gene expression can be confirmed by measuring the amount of RNA which is produced by ydhL gene expression in the bacterium of the present invention by northern hybridization or RT-PCR (Molecular cloning: Cold spring Harbor Laboratory Press, Cold Spring Harbor (USA), 2001), and comparing it to that of a wild-type or non-modified strain. The expression of the ydhL gene in the microorganism of the present invention is enhanced more than that of a wild-type or non-modified strain, and preferably not less than 1.5-fold, more preferably not less than 2-fold, and most preferably not less than 3-fold when compared to expression of the ydhL gene in a wild-type or non-modified strain.

The bacterium of the present invention is a bacterium belonging to either the genus *Bacillus* or *Escherichia*. An example of the microorganism belonging to the genus *Escherichia* which can be used in the present invention is

*Escherichia coli* (*E. coli*). Examples of the microorganism belonging to the genus *Bacillus* which can be used in the present invention include *Bacillus subtilis* subsp. *subtilis* str. 168 (*B. subtilis* 168) or *Bacillus amyloliquefaciens* (*B. amyloliquefaciens*).

Examples of bacteria belonging to genus *Bacillus* also include the following:
Bacillus lichenifonnis
Bacillus pumilis
Bacillus megaterium
Bacillus brevis
Bacillus polymixa
Bacillus stearothermophilus.

Bacteria belonging to genus of *Escherichia* reported in Neidhardt et al. (Neidhardt, F. C. et al., *Escherichia coli* and *Salmonella Typhimurium*, American Society for Microbiology, Washington D.C., 1208, Table 1), such as *Escherichia coli*, can be utilized. Examples of wild-type strains of *Escherichia coli* include, but are not limited to, the K12 strain and derivatives thereof, *Escherichia coli* MG1655 strain (ATCC No. 47076), and W3110 strain (ATCC No. 27325). These strains are available from the American Type Culture Collection (ATCC, Address: P.O. Box 1549, Manassas, Va. 20108, United States of America).

In addition to the properties already mentioned, the bacteria of the present invention may have other specific properties such as various nutrient requirements, drug resistance, drug sensitivity, and drug dependence without departing from the scope of the present invention.

The phrase "purine nucleoside" as used herein includes inosine, xanthosine, guanosine, and adenosine, preferably inosine.

The phrase "purine-nucleoside producing ability" as used herein means an ability to produce and cause accumulation of a purine nucleoside in a medium. The phrase "having purine-nucleoside producing ability" means that the microorganism belonging to the genus *Escherichia* or *Bacillus* is able to produce and cause accumulation of purine nucleosides in a medium in an amount larger than a wild-type strain of *E. coli*, such as *E. coli* W3110 and MG1655, or a wild-type strain of *B. subtilis* such as *B. subtilis* 168. Preferably this phrase means that the microorganism is able to produce and cause accumulation in a medium in an amount of not less than 10 mg/l, more preferably not less than 50 mg/l of inosine, xanthosine, guano sine or/and adeno sine.

As used herein, when an activity of a protein of the present invention is enhanced in a bacterium, this means that the number of the protein molecules in the bacterium is increased, or that the activity per protein molecule itself is increased.

The term "orthologous gene" or an "ortholog" means a gene from one species which corresponds to a gene in another species that is related via a common ancestral species (a homologous gene), but which has evolved to become different from the gene of the other species. Orthologous genes may or may not have the same function. If complete genomes of organisms are sequenced, the following technique could be used to search for orthologs. A BLAST search is performed using a gene from one organism to find the best homolog in the other organism. Then the second backward BLAST search is performed using the best homolog from the other organism found in the first round of BLAST search to find the best homolog or ortholog in the first organism. If the gene used in the first round and the gene found in the second round coincide, the gene from first organism and the best homolog in the other organism are orthologs. In the process of the BLAST search, the homology of proteins coded by the genes of interest is determined.

For the purpose of the present invention, proteins encoded by orthologous gene are homologous proteins having the same activity. Searching for such orthologs is performed by determining the sequence of genes and proteins, and activity of proteins (see, for example, FIG. 1 and Example 2).

The gene coding for the YdhL protein of *Bacillus amyloliquefaciens*, the ydhL gene, has been sequenced (SEQ ID NO: 1). The gene coding for YdhL protein from *Bacillus subtilis*, ydhL gene of *Bacillus subtilis* subsp. *subtilis* str. 168, has been elucidated (numbers from 13042 to 14208 in EMBL accession number Z99107) (SEQ ID NO: 3). The ydhL gene from *Bacillus subtilis* is located on the chromosome between ydhK and ydhM genes at 53.50°. Therefore, said ydhL genes can be obtained by PCR (polymerase chain reaction; refer to White, T. J. et al., *Trends Genet.*, 5, 185 (1989)) utilizing primers prepared based on the nucleotide sequence of the gene. Genes coding for YdhL protein from other microorganisms can be obtained in a similar manner (see Example 2).

The ydhL gene derived from *Bacillus amyloliquefaciens* can be also exemplified by a DNA which encodes the proteins of the present invention, such as a protein which has the amino acid sequence shown in SEQ ID NO: 2, and/or a protein which has the amino acid sequence of SEQ ID NO: 2, but which includes the deletion, substitution, insertion or addition of one or several amino acids, and which has an activity of making a bacterium belonging to the genus *Bacillus* or to the genus *Escherichia* resistant to purine base analogues and/or purine nucleosides such as inosine and guanosine, when the activity of the protein is enhanced in the bacterium. An example of the DNA is SEQ ID NO: 1.

The ydhL gene derived from *Bacillus subtilis* encompasses a DNA which encodes the proteins of the present invention including a protein which has the amino acid sequence shown in SEQ ID NO: 4, and/or a protein which has the amino acid sequence of SEQ ID NO: 4, but includes the deletion, substitution, insertion or addition of one or several amino acids, and which has an activity of making a bacterium belonging to the genus *Bacillus* or to the genus *Escherichia* resistant to purine base analogues and purine nucleosides such as inosine and guanosine, when the activity of the protein is enhanced in the bacterium. An example of the DNA is SEQ ID NO: 3.

The DNAs which encode substantially the same proteins as the YdhL proteins described above may be obtained, for example, by modifying the nucleotide sequence of the DNA encoding the YdhL proteins, for example, by means of site-directed mutagenesis so that one or more amino acid residues at a specified site are deleted, substituted, inserted, or added. DNA modified as described above may be obtained by conventionally known mutation treatments. Such treatments include hydroxylamine treatment of the DNA encoding proteins of present invention, or treatment of the bacterium containing the DNA with UV irradiation or a reagent such as N-methyl-N'-nitro-N-nitrosoguanidine or nitrous acid.

A DNA encoding substantially the same protein as the YdhL protein derived from *Bacillus amyloliquefaciens* can be obtained by expressing the DNA having mutations as described above in an appropriate cell, and investigating the activity of any expressed product. A DNA encoding substantially the same protein as the YdhL protein can also be obtained by isolating a DNA from mutant DNA encoding the YdhL protein or from a mutant-containing cell, wherein the DNA is hybridizable with a probe having a nucleotide sequence which contains, for example, the nucleotide sequence shown as SEQ ID NO: 1, under stringent conditions, and encodes a protein having the activity of the YdhL protein. The "stringent conditions" referred to herein are conditions under which so-called specific hybrids are formed, and non-specific hybrids are not formed. It is difficult to clearly express this condition by using any numerical value. However, for example, the stringent conditions include conditions under which DNAs which are highly homologous, for example, DNAs having homology of not less than 50%, preferably not less than 70%, more preferably not less than 90%, still more preferably not less than 95% are able to hybridize with each other, but DNAs having homology lower than the above are not able to hybridize with each other. Alternatively, the stringent conditions may be exemplified by conditions under which DNA is able to hybridize at a salt concentration equivalent to typical washing conditions in Southern hybridization, i.e., approximately 1×SSC, 0.1% SDS, preferably 0.1×SSC, 0.1% SDS, at 60° C. Duration of washing depends on the type of membrane used for blotting and, as a rule, is recommended by manufacturer. For example, recommended duration of washing the Hybond™ N+nylon membrane (Amersham) under stringent conditions is 15 minutes. Preferably, washing may be performed 2 to 3 times.

A partial sequence of the nucleotide sequence of SEQ ID NO: 1 can also be used as a probe. Probes may be prepared by PCR using primers based on the nucleotide sequence of SEQ ID NO: 1, and a template which contains a DNA having the nucleotide sequence of SEQ ID NO: 1. When a DNA fragment having a length of about 300 bp is used as the probe, the hybridization conditions for washing might be, for example, 50° C., 2×SSC and 0.1% SDS.

All of the above is applicable for the YdhL protein and ydhL gene derived from *Bacillus subtilis*.

Techniques for enhancing the activity of the protein of present invention, especially techniques for increasing the number of protein molecules in a bacterial cell, include altering the expression regulatory sequence of a DNA coding for the protein of the present invention, and increasing the copy number of the gene, but are not limited thereto.

Altering the expression regulatory sequence of a DNA coding for the protein of present invention can be achieved by locating the DNA coding for the protein of present invention under the control of a strong promoter. For example, lac promoter, trp promoter, trc promoter, P$_L$ promoter of lambda phage are all known strong promoters for *E. coli*. Especially, veg promoter, spac promoter, xylE promoter are known as strong promoters for *Bacillus*. Alternatively, a promoter's activity can be enhanced by, for example, introducing a mutation into the promoter to increase the transcription level of a gene located downstream of the promoter (WO00/18935). Furthermore, the mRNA translatability can be enhanced by introducing a mutation into a spacer region between the ribosome binding site (RBS) and the start codon. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984).

Furthermore, to increase the transcription level of the gene, an enhancer may be newly introduced. The introduction of DNA containing either a gene or promoter into chromosomal DNA is described in, for example, Japanese Patent Application Laid-Open No. 1-215280 (1989).

Alternatively, the copy number of the gene may be increased by inserting the gene into a multi-copy vector to form a recombinant DNA, followed by introduction of the recombinant DNA into a microorganism. Examples of vectors autonomously replicable in *Escherichia coli* include pUC19, pUC18, pHSG299, pHSG399, pHSG398, pACYC184, (pHSG and pACYC are available from Takara Bio), RSF1010, pBR322, pMW219 (pMW is available from Nippon Gene), and so forth. Examples of vectors which are autonomously replicable in *Bacillus* bacteria include pUB10, pC194, pE194. Preferably, low-copy vectors are used. Examples of low-copy vectors include but are not limited to pSC101, pMW118, pMW119, and the like. The term "low-copy vector" is used for vectors which result in a copy number of up to 5 copies per cell. Methods of transformation include any known methods in the art. For example, a method of treating recipient cells with calcium chloride so as to increase permeability of the cells to DNA has been reported for *Escherichia coli* K-12 (Mandel, M. and Higa, A., J. Mol. Biol., 53, 159 (1970)) and may be used in the present invention.

Enhancement of gene expression may also be achieved by introducing multiple copies of the gene into the bacterial chromosome via, for example, homologous recombination, Mu integration, or the like. For example, one act of Mu integration permits introduction into the bacterial chromosome of up to 3 copies of the gene.

The techniques described above of using a strong promoter or enhancer can be combined with the techniques based on increasing the copy number or expression of the gene.

Ordinary methods known in the art for preparation of chromosomal DNA, hybridization, PCR, preparation of plasmid DNA, digestion and ligation of DNA, transformation, selection of an oligonucleotide as a primer and the like may be used in the present invention. These methods are described in Sambrook, J., and Russell D., "Molecular Cloning A Laboratory Manual, Third Edition", Cold Spring Harbor Laboratory Press (2001) and the like.

To breed a microorganism belonging to the genus *Bacillus* which results in increased expression of the gene or genes coding for the protein or proteins of the present invention, necessary regions of the gene or genes may be obtained by PCR (polymerase chain reaction), primarily based on available information about the *B. subtilis* genes. For example, ydhL gene, which seems to be a gene coding for a transporter, can be cloned from the chromosomal DNA of *B. subtilis* strains using PCR. The chromosomal DNA used for this may be derived from any other strain of *B. subtilis*.

The protein of present invention includes mutants and variants of the YdhL protein which exist due to natural diversity, and homologous proteins of YdhL which are present in different bacteria, provided these mutant, variant, or homologous proteins demonstrate the functional property of the YdhL protein, that is, imparting resistance to purine base analogues and purine nucleosides such as inosine, or guanosine.

The bacterium of the present invention can be obtained by introducing the aforementioned DNAs coding for the proteins of present invention into a bacterium inherently having an ability to produce purine nucleosides such as inosine. Alternatively, the bacterium of present invention can be obtained by imparting an ability to produce purine nucleosides such as inosine to a bacterium already harboring the DNAs.

An example of the parent strain belonging to the genus *Bacillus* that may be used in the present invention is the *B. subtilis* strain KMBS16-1. This strain is a derivative of the inosine-producing strain *B. subtilis* KMBS16 in which a purA::erm mutation was changed to a purA::cat mutation. In turn, *B. subtilis* KMBS16 is a derivative of the known *B. subtilis* trpC2, which has mutations introduced into the purA gene coding for succinyl-AMP synthase (purA::erm), the purR gene coding for a purine repressor (purR::spc), and the deoD gene coding for purine nucleoside phosphorylase (deoD::kan) (US 2004-0166575A). Other parent strains belonging to the genus *Bacillus* that may be used in the present invention include *B. subtilis* strain AJ12707 (FERM P-12951) (Japanese Patent Application JP6113876A2), *B. subtilis* strain AJ3772 (FERM P-2555) (Japanese Patent Application JP62014794A2), 6-ethoxypurine-resistant strain AJ13937 (FERM BP-18665) (US2004-0166575), or the like An example of an inosine-producing strain belonging to the genus *Escherichia* is FADRaddedd(pMWKQ). This strain is a derivative of the known strain W3110, which has mutations introduced into the purF gene coding for PRPP amidotransferase, the purR gene coding for a purine repressor, the deoD gene coding for purine nucleoside phosphorylase, the purA gene coding for succinyl-AMP synthase, the add gene coding for adenosine deaminase, the edd gene coding for 6-phosphogluconate dehydrase (WO9903988), and harbors the pMWKQ plasmid, which contains the purFKQ gene coding for the PRPP amidotransferase and is insensitive to GMP (WO9903988).

Moreover, the examples also include releasing regulation of an enzyme involved in inosine biosynthesis, specifically, a method of canceling feedback inhibition of such an enzyme (WO99/03988). Examples of the means for canceling regulation of such an enzyme as mentioned above involved in the inosine biosynthesis include, for example, deletion of the purine repressor (U.S. Pat. No. 6,284,495). Examples of the method of deleting the purine repressor include disrupting a gene coding for the purine repressor (purR, GenBank Accession No. Z99104).

Moreover, the inosine-producing ability can also be increased by blocking a reaction branching off from the inosine biosynthesis pathway, which results in another metabolic product (WO99/03988). Examples of a reaction branching off from the inosine biosynthesis pathway and resulting in another metabolic product include reactions catalyzed by, for example, succinyl-adenosine monophosphate (AMP) synthase, inosine-guanosine kinase, 6-phosphogluconate dehydrase, phosphoglucoisomerase, and so forth. The succinyl-adenosine monophosphate (AMP) synthase is encoded by purA (GenBank Accession No. Z99104).

Furthermore, the inosine-producing ability can also be enhanced by weakening incorporation of inosine into cells. The incorporation of inosine into cells can be weakened by blocking a reaction involved in the incorporation of inosine into cells. Examples of the aforementioned reaction involved in the incorporation of the inosine into cells include a reaction catalyzed by, for example, nucleoside permease.

To increase the activity per protein molecule in the protein of the present invention, it is also possible to introduce a mutation into the structural gene of the protein to enhance the activity of the protein. In order to introduce a mutation into the gene, site-specific mutagenesis (Kramer, W. and Frits, H. J., Methods in Enzymology, 154, 350 (1987)), recombinant PCR (PCR Technology, Stockton Press (1989)), chemical synthesis of a specific portion of the DNA, hydroxylamine treatment of the gene of interest, treatment of microbial strains having the gene of interest by UV irradiation or a chemical agent such as nitrosoguanidine or nitrous acid, and the like can be used. A microorganism in which the activity of the protein is enhanced can be selected as a strain growing in a minimal medium containing 8-azaadenine, 6-methylpurine, 2,6-diaminopurine, 6-mercaptopurine, 8-azaguanine, or inosine in concentrations shown in Table 1 (see below).

The bacterium of the present invention may be further improved by enhancing the expression of one or more genes involved in purine biosynthesis. Such genes include the pur regulon of *E. coli* (*Escherichia coli* and *Salmonella*, Second Edition, Editor in Chief: F. C. Neidhardt, ASM Press, Washington D.C., 1996). The inosine-producing *E. coli* strain having a mutant purF gene encoding a PRPP amidotransferase not subject to feedback inhibition by ADP and GMP, and an inactivated purR gene encoding the repressor in the purine nucleotide biosynthesis system has been described. (WO9903988).

III. Method for Producing Purine Nucleosides

The method of the present invention includes a method for producing purine nucleosides including the steps of cultivating the bacterium of the present invention in a culture medium, allowing the purine nucleosides to be produced and secreted by the bacterium, and collecting the purine nucleosides from the culture medium. Furthermore, the method of the present invention includes a method for producing inosine including the steps of cultivating the bacterium of the present invention in a culture medium, allowing inosine to be produced and secreted by the bacterium, and collecting inosine from the culture medium. Furthermore, the method of the present invention includes a method for producing xanthosine including the steps of cultivating the bacterium of the present invention in a culture medium, allowing xanthosine to be produced and secreted by the bacterium, and collecting xanthosine from the culture medium. Furthermore, the method of the present invention includes a method for producing guanosine including the steps of cultivating the bacterium of the present invention in a culture medium, allowing guanosine to be produced and secreted by the bacterium, collecting guanosine from the culture medium.

In the present invention, the cultivation, collection, and purification of purine nucleoside from the medium and the like may be performed in a manner similar to conventional fermentation methods wherein a purine nucleoside is produced using a microorganism. Culture medium for purine nucleoside production may be a typical medium containing a carbon source, a nitrogen source, inorganic ions, and other organic components as required. As the carbon source, saccharides such as glucose, lactose, sucrose, galactose, fructose, arabinose, maltose, xylose, trehalose, ribose and hydrolyzates of starches; alcohols such as glycerol, mannitol and sorbitol; organic acids such as gluconic acid, fumaric acid, citric acid and succinic acid and the like can be used.

As the nitrogen source, inorganic ammonium salts such as ammonium sulphate, ammonium chloride, and ammonium phosphate; organic nitrogen such as of soybean hydrolyzates; ammonia gas; aqueous ammonia and the like can be used. It is desirable that vitamins such as vitamin B1, required substances, for example, nucleic acids such as adenine and RNA, or yeast extract and the like are contained in appropriate amounts as trace organic nutrients. Other than these, small amounts of calcium phosphate, magnesium sulphate, iron ions, manganese ions and the like may be added, if necessary.

Cultivation is preferably performed under aerobic conditions for 16 to 72 hours, and the culture temperature during the cultivation is controlled within 30 to 45° C. and the pH between 5 and 8. The pH can be adjusted by using an inorganic or organic acidic or alkaline substance as well as ammonia gas.

After cultivation, solids such as cells can be removed from the liquid medium by centrifugation or membrane filtration, and then the target purine nucleoside can be recovered from the fermentation liquor by any of a combination of conventional techniques, such as ion exchange resins and precipitation.

4. Method for Producing Purine Nucleotides

The method of the present invention includes a method for producing purine nucleotides including the steps of cultivating the bacterium of the present invention in a culture medium, phosphorylating the desired purine nucleoside to generate a purine nucleotide corresponding to the purine nucleoside, optionally allowing secretion of the purine nucleotide into the culture medium by the bacterium, and collecting the purine nucleotide. Furthermore, the method of the present invention includes a method for producing 5'-inosinic acid including the steps of cultivating the bacterium of the present invention in a culture medium, phosphorylating inosine to generate 5'-inosinic acid, optionally allowing secretion of 5'-inosinic acid into the culture by the bacterium, and collecting 5'-inosinic acid. Furthermore, the method of the present invention includes a method for producing 5'-xanthylic acid including the steps of cultivating the bacterium of the present invention in a culture medium, phosphorylating xanthosine to generate 5'-xanthylic acid, optionally allowing secretion of 5'-xanthylic acid into the culture medium by the bacterium, and collecting 5'-xanthylic acid. Furthermore, the method of the present invention includes a method for producing 5'-guanylic acid including the steps of cultivating the bacterium of the present invention in a culture medium, phosphorylating guanosine to generate 5'-guanylic acid, optionally allowing secretion of 5'-guanylic acid into the culture medium by the bacterium, and collecting 5'-guanylic acid. And the method of the present invention includes a method for producing 5'-guanylic acid including the steps of cultivating the bacterium of the present invention in a culture medium, phosphorylating xanthosine to generate 5'-xanthylic acid, optionally allowing secretion of 5'-xanthylic acid into the culture medium by the bacterium, aminating 5'-xanthylic acid to generate 5'-guanylic acid, and collecting 5'-guanylic acid.

In the present invention, the cultivation, collection, and purification of inosine from the medium and the like may be performed in a manner similar to conventional fermentation methods wherein inosine is produced using a microorganism. Furthermore, in the present invention, the steps of phosphorylating inosine, optionally allowing secretion into the culture medium by the bacterium, and collecting 5'-inosinic acid may be performed in a manner similar to conventional fermentation methods wherein a purine nucleotide such as 5'-inosinic acid is produced from a purine nucleoside such as inosine.

The phosphorylation of the purine nucleoside could be performed enzymatically using different phosphatases, nucleoside kinases, or nucleoside phosphotransferases, or chemically using phosphorylating agents such as $POCl_3$ or the like. A phosphatase which is able to catalyze the C-5'-position selective transfer of a phosphoryl group of pyrophosphate to nucleosides (Mihara et. al, Phosphorylation of nucleosides by the mutated acid phosphatase from *Morganella morganii*. Appl. Environ. Microbiol., 66:2811-2816 (2000)) or acid phosphatase utilizing the poly-phosphoric acid (salts), phenylphosphoric acid (salts) or carbamylphosphoric acid (salts) as a phosphoric acid donor (WO9637603A1) or the like may be used. Also, as an example of phosphatase, the phosphatase which is able to catalyze the transfer of a phosphoryl group to the C-2', 3', or 5'-position of nucleosides utilizing the p-nitrophenyl phosphate (Mitsugi, K., et al, Agric. Biol. Chem., 28, 586-600 (1964)), inorganic phosphate (Japanese Patent Application Nos or Japanese Patent Application Laid-Open No. JP42-1186) or acetyl phosphate (Japanese Patent Application Nos or Japanese Patent Application Laid-Open No. JP61-41555) as a substrate, or the like may be used. As an example of nucleoside kinase, guanosine/inosine kinase from *E. coli* (Mori, H. et. al. Cloning of a guanosine-inosine kinase gene of *Escherichia coli* and characterization of the purified gene product. J. Bacteriol. 177:4921-4926 (1995); WO9108286) or the like may be used. As an example of nucleoside phosphotransferase, the nucleoside phosphotransferases described by Hammer-Jespersen, K. (Nucleoside catabolism, p. 203-258. In A Munch-Petesen (ed.), Metabolism of nucleotides, nucleosides, and nucleobases in microorganism. 1980, Academic Press, New York) or the like may be used. The chemical phosphorylation of nucleosides may be performed using a phosphorylation agent such as $POCl_3$ (Yoshikawa, K. et. al. Studies of phosphorylation. III. Selective phosphorylation of unprotected nucleosides. Bull. Chem. Soc. Jpn. 42:3505-3508 (1969)) or the like.

The amination of the 5'-xanthylic acid can be performed enzymatically using, for example, GMP synthetase from *E. coli* (Fujio et. al. High level of expression of XMP aminase in *Escherichia coli* and its application for the industrial production of 5'-guanylic acid. Biosci. Biotech. Biochem. 1997, 61:840-845; EP0251489B1).

EXAMPLES

The present invention will be more concretely explained below with reference to the following non-limiting examples.

Example 1

Cloning of the ydhL Gene of *B. Subtilis*

The entire nucleotide sequence of *B. subtilis* subsp. *subtilis* strain 168 has been determined (Kunst et al., Nature 390, 249-256 (1997)). Based on the reported nucleotide sequence, primers ydhL_N (SEQ ID No. 5) and ydhL_C (SEQ ID NO: 6) were synthesized and used to amplify the ydhL gene from *B. subtilis* strain 168 via PCR. The primer ydhL_N is identical to the sequence from 489 to 467 bp, which is upstream of the start codon of the ydhL gene, and having the restriction enzyme SalI recognition site introduced at the 5'-end thereof. The primer ydhL_C is complementary to a sequence from 58 to 80 bp, which is downstream of the termination codon of the ydhL gene, and having the restriction enzyme BglII recognition site introduced at the 5'-end thereof.

The chromosomal DNA of *B. subtilis* strain 168 was prepared by ordinary methods. PCR was carried out on a "Perkin Elmer GeneAmp PCR System 2400" under the following conditions: 30 sec. at 94° C., 45 sec. at 61° C., 3 min at 72° C., 25 cycles by means of PfuI polymerase (Fermentas). The resulting PCR fragment containing the ydhL gene with its own promoter was treated with BglI and SalI and inserted into the low copy-number vector pMW118, which had been previously treated with the BamHI and SalI enzymes. Thus, the plasmid pYDHL1 was obtained.

The pYDHL1 plasmid and the vector were used to transform the *E. coli* strain TG1 (Amersham Pharmacia Biotech) via standard techniques. Transformants were selected on L-broth agar plates with 100 μg/ml ampicillin. Thus, the *E. coli* strains TG1 (pYDHL1) and TG1 (pMW118) were obtained. Then the ability of these strains to grow in the presence of purine base analogues was determined on M9 glucose minimal agar plates containing graded concentrations of an inhibitor. The plates were spotted with $10^5$ to $10^6$ cells from an overnight culture grown in a minimal medium (supplemented with 100 μg/ml of ampicillin). The growth was estimated after 44 h incubation at 37° C.

The results are presented in Table 1.

TABLE 1

| Strain | Growth on the minimal medium containing | | | |
|---|---|---|---|---|
| | - | DAP, 400 µg/ml | MP, 400 µg/ml | AzaA, 300 µg/ml | DAP, 400 µg/ml + MP, 400 µg/ml |
| TG1 (pMW118) | + | − | − | − | − |
| TG1 (pYDHL1) | + | + | + | + | + |

Note.
DAP: 2,6-diaminopurine; MP: 6-mercaptopurine; AzaA: 8-azaadenine; +: good growth; −: no growth. Good growth means that the size of colonies which grew on the medium with purine analogues did not differ significantly from the size of colonies of the control strain which grew on the medium without purine analogues.

It can be seen from Table 1 that the ydhL gene amplification increased the resistance of the bacteria to 2,6-diaminopurine, 6-mercaptopurine, and 8-azaadenine.

The pYDHL1 plasmid and the pMW118 vector were also transformed into the E. coli strain TG1 deoD gsk3. The E. coli strain TG1 deoD gsk3 was an especially constructed parental strain which is used for checking the resistance to inosine and guanosine. This strain was obtained by sequential introduction of a deoD mutation, as described in PCT application WO9903988 and gsk3 mutation described by Petersen C. (J. Biol. Chem., 274, 5348-5356, 1999) using phage P1-mediated transduction into the known strain TG1 (VKPM B-5837), which is resistant to inosine and guanosine due to its ability to degrade purine. The strain TG1 deoD gsk3 cannot degrade guanosine and inosine due to a deoD mutation (WO9903988), and it is sensitive to nucleosides due to a gsk3 mutation (Petersen C. J. Biol. Chem., 274, 5348-5356, 1999). Thus, the strains TG1 deoD gsk3 (pYDHL1) and TG1 deoD gsk3 (pMW118) were obtained. Then the ability of these strains to grow in the presence of inosine and guanosine was determined as above.

The results are presented in Table 2.

TABLE 2

| Strain | Growth on the minimal medium containing | | | |
|---|---|---|---|---|
| | Inosine | | Guanosine | |
| | 300 mg/l | 1000 mg/l | 10 mg/l | 15 mg/l |
| E. coli deoD gsk3 (pMW118) | − | − | − | − |
| E. coli deoD gsk3 (pYDHL1) | + | + | + | − |

Note.
+: good growth; −: no growth.

It follows from the Table 2 that ydhL gene overexpression conferred a high-level resistance to inosine and a low-level resistance to guanosine. Therefore, it can be predicted that the ydhL gene is involved in the secretion of purine nucleosides, and more specifically, in the secretion of inosine.

Example 2

Cloning of the ydhL Gene of *Bacillus amyloliquefaciens*

The data presented in Example 1 show that overexpression of the ydhL gene of *B. subtilis* (hereafter: ydhL$_{Bs}$) conferred upon cells resistance to 2,6-diaminopurine and 6-mercaptopurine when introduced simultaneously into M9 glucose minimal agar (Table 1). On the basis of this fact, the cloning of an ortholog of the ydhL$_{Bs}$ gene from *B. amyloliquefaciens* (hereafter: ydhL$_{Ba}$) was performed. The chromosomal DNA of *B. amyloliquefaciens* strain BA1(IAM1523) was prepared by ordinary methods. The chromosomal DNA was cut with EcoRI and ligated with the pMW118 vector which had been previously treated with the same enzyme. The resulting DNA was used to transform *E. coli* strain TG1. Transformants were selected on minimal agar containing 400 µg/ml 2,6-diaminopurine, 400 µg/ml 6-mercaptopurine, and 100 µg/ml ampicillin. Plasmid DNA was isolated from the transformants and analyzed. From these, the hybrid plasmid pYDHL2 containing a minimal inserted DNA fragment of about 1.6 kb was found. In contrast to the ydhL$_{Bs}$ gene it contained no EcoRI site. The inserted fragment was sequenced from the universal primers, and was found to have high homology (more then 90%) with the ydhL$_{Bs}$ gene (FIG. 1). The new gene from *B. amyloliquefaciens* was named ydhL gene (hereinafter, also labelled as ydhL$_{Ba}$ gene). When introduced into the TG1 and TG1 deoD gsk3 strains, the pYDHL2 plasmid conferred upon cells resistance to purine base analogues and nucleosides, respectively, in the same way as the pYDHL1 plasmid did. It was concluded that the pYDHL2 plasmid indeed contains the ydhL$_{Ba}$ gene.

Example 3

Effect of Amplification of the ydhL$_{Bs}$ and ydhL$_{Ba}$ Genes on Inosine Production by the *E. coli* Inosine-Producing Strain The inosine-producing *E. coli* strain FADRaddedd (pMWKQ) was transformed with each of the pMW18 vector, the YDHL1 plasmid, and the pYDHL2 plasmid. The transformants were selected on L-agar containing 100 mg/l ampicillin and 75 mg/l kanamycin. Thus, the strain FADRaddedd (pMWKQ, pMW18), FADRaddedd (pMWKQ, pYDHL1), and FADRaddedd (pMWKQ, pYDHL2) were obtained. These strains were each cultivated at 37° C. for 18 hours in L-broth with 100 mg/l ampicillin and 75 mg/l kanamycin, and 0.3 ml of the obtained culture was inoculated into 3 ml of a fermentation medium containing 100 mg/l ampicillin and 75 mg/l kanamycin, in a 20×200 mm test tube, and cultivated at 37° C. for 72 hours with a rotary shaker.

The composition of the fermentation medium (g/l):

| | |
|---|---|
| Glucose | 40.0 |
| (NH$_4$)$_2$SO$_4$ | 16.0 |
| K$_2$HPO$_4$ | 0.1 |
| MgSO$_4$•7H$_2$O | 1.0 |
| FeSO$_4$•7H$_2$O | 0.01 |
| MnSO$_4$•5H$_2$O | 0.01 |
| Yeast extract | 8.0 |
| CaCO$_3$ | 30.0 |

Glucose and magnesium sulphate are sterilized separately. CaCO$_3$ is dry-heat sterilized at 180° C. for 2 hours. pH is adjusted to 7.0. Antibiotic is introduced into the medium after sterilization.

After the cultivation, the amount of inosine which accumulated in the medium was determined by HPLC. A sample of the culture medium (500 µl) is centrifuged at 15,000 rpm for 5 minutes, and the supernatant is diluted 4 times with H$_2$O and analyzed by HPLC.

Conditions for HPLC Analysis:
Column: Luna C18(2) 250×3 mm, 5u (Phenomenex, USA). Buffer: 2% v/v C$_2$H$_5$OH; 0.8% v/v thriethylamine;

0.5% v/v acetic acid (glacial); pH 4.5. Temperature: 30° C. Flow rate: 0.3 ml/min. Injection volume: 5 μl. Detection: UV 250 nm.

Retention time (min):

| | |
|---|---|
| Xanthosine | 13.7 |
| Inosine | 9.6 |
| Hypoxanthine | 5.2 |
| Guanosine | 11.4 |
| Adenosine | 28.2 |

The results are presented in Table 3.

TABLE 3

| Strain | $OD_{540}$ | Inosine, g/l |
|---|---|---|
| E. coli FADRaddedd (pMWKQ, pMW118) | 9.0 | 1.5 ± 0.2 |
| E. coli FADRaddedd (pMWKQ, pYDHL1) | 8.6 | 2.3 ± 0.2 |
| E. coli FADRaddedd (pMWKQ, pYDHL2) | 8.4 | 2.2 ± 0.2 |

As it is seen from the Table 3, the overexpression of $ydhL_{Bs}$ and $ydhL_{Ba}$ genes improved inosine productivity of the FADRaddedd (pMWKQAp) strain.

Example 4

Cloning the $ydhL_{Bs}$ gene into a low-copy number shuttle vector pMWMX1

The PCR fragment containing the $ydhL_{Bs}$ gene under the control of its own promoter (obtained in Example 1) was treated with BglI and SalI and inserted into low-copy number shuttle vector pMWMX1, which had been previously treated with the BamHI and SalI enzymes. Thus, the plasmid pYDHL3 was obtained. The pMWMX1 vector (FIG. 2) is a derivative of two low-copy-number plasmids: pMW118 and pMX30. The pMX30 plasmid (Rabinovich et al., Mol. Biol. (Moscow), 18, 189-196, 1984) in turn, is a deletion derivative of pSM19035, a broad-host-range plasmid of the inc18 family (Brantl et al., Nucleic Acids Res., 18, 4783-4790). The pMW118 and pMX30 plasmids were each cut with EcoRI and ligated. Thus the vector pMWMX1 was obtained.

Example 5

Construction of the Low-Copy Number Shuttle Plasmid pYDHL3 Containing the $ydhL_{Ba}$ Gene The pYDHL2 plasmid was partially cut with EcoRI to obtain a single fragment, and ligated with pMX30 which had been cut with the same enzyme. Thus, a shuttle plasmid pYDHL4 containing the $ydhL_{Ba}$ gene was obtained. Therefore, the pYDHL4 plasmid is equivalent to pYDHL3 plasmid, except for the replacement of the pMWMX1 vector containing the $ydhL_{Bs}$ gene with the $ydhL_{Ba}$ gene.

Example 6

Effect of the Amplification of $ydhL_{Bs}$ or $ydhL_{Ba}$ Genes on Resistance of the B. subtilis Strain 168 to Purine Base Analogues The pYDHL3, pYDHL4 plasmids and the pMWMX1 vector were used to transform wild-type B. subtilis strain 168 via standard techniques. Transformants were selected on L-broth agar plates with 10 μg/ml erythromycin. Thus, the strains B. subtilis 168(pMWMX1), B. subtilis 168(pYDHL3) and B. subtilis 168(pYDHL4) were obtained. Then, the ability of these strains to grow in the presence of purine base analogues was determined on M9 glucose minimal agar plates (minimal medium M9, glucose-2%, vitamin assay casamino acids (Difco)—0.1%, tryptophan—100 μg/ml) containing graded concentrations of a purine analogue. The plates were spotted with $10^5$ to $10^6$ cells from an overnight culture grown on the above agar plates without the analogues. The growth was estimated after 48 h incubation at 34° C.

The results are presented in Table 4.

TABLE 4

| | Growth on the minimal medium containing | | | | |
|---|---|---|---|---|---|
| Strain | - | AzaG, 2 μg/ml | AzaG, 10 μg/ml | MePur, 20 μg/ml | AzaA, 2 mg/ml |
| B. subtilis 168 | + | – | – | – | – |
| B. subtilis 168(pYDHL3) | + | + | n.d. | + | n.d. |
| B. subtilis 168(pYDHL4) | + | + | + | + | + |

Note:
AzaG—8-azaguanine; MePur—6-methylpurine; AzaA—8-azaadenine; n.d.—no data; +: good growth; –: no growth. Good growth means that size of colonies grown on the medium with purine analogues did not differ significantly from size of colonies of the control strain grown on the medium without purine analogues.

It can be seen from Table 4 that the amplification of the $ydhL_{Bs}$ or $ydhL_{Ba}$ genes increased resistance of the bacteria to 8-azaguanine, 6-methylpurine, and 8-azaadenine.

Example 7

Effect of Amplification of the $ydhL_{Bs}$ or $ydhL_{Ba}$ Genes on Inosine Production by the B. subtilis Inosine-Producing Strain.

The inosine-producing B. subtilis strain KMBS16-1 was transformed with the pMWMX1 vector, pYDHL3, or pYDHL4 plasmids. Thus, the strains B. subtilis KMBS16-1 (pMWMX1), B. subtilis KMBS16-1(pYDHL3), and B. subtilis KMBS16-1(pYDHL4) were obtained. These strains were each cultivated at 37° C. for 18 hours in L-broth with 10 mg/l erythromycin. 0.3 ml of the resulting culture was inoculated into 3 ml of a Bacillus fermentation medium containing 10 mg/l erythromycin, in a 20×200 mm test tube, and cultivated at 37° C. for 72 hours with a rotary shaker.

The composition of the Bacillus fermentation medium: (g/l)

| | |
|---|---|
| Glucose | 80.0 |
| $KH_2PO_4$ | 1.0 |
| $MgSO_4$ | 0.4 |
| $FeSO_4 \cdot 7H_2O$ | 0.01 |
| $MnSO_4 \cdot 5H_2O$ | 0.01 |
| Mameno (soybean hydrolysate) | 1.35 of TN (total nitrogen) |
| DL-Methionine | 0.3 |
| $NH_4Cl$ | 32.0 |
| Adenine | 0.1 |
| Tryptophan | 0.02 |
| $CaCO_3$ | 50.0 |

After the cultivation, the amount of inosine which had accumulated in the medium was determined by HPLC as above. The results are presented in Table 5.

TABLE 5

| Strain | OD$_{540}$ | Inosine, g/l |
|---|---|---|
| B. subtilis KMBS16-1 (pMWMX1) | 8.4 | 1.4 ± 0.1 |
| B. subtilis KMBS16-1 (pYDHL3) | 8.2 | 1.6 ± 0.2. |
| B. subtilis KMBS16-1 (pYDHL4) | 8.0 | 1.7 ± 0.2 |

As it is seen from the Table 5, the amplification of either of the ydhL$_{Bs}$ or ydhL$_{Ba}$ genes improved inosine productivity of the B. subtilis strain KMBS16-1.

Example 8

Modification of the Regulatory Region of the B. amyloliquefaciens ydhL Gene

It is known that modification of the B. subtilis ydhL regulatory region, namely modification of the G-box of 5'-untranslated RNA region, may increase expression of the gene (Mandal, M. and Breaker, R. R., Nat. Struct. Mol. Biol., 11 (1), 29-35 (2004)). Therefore, to enhance the ydhL gene expression level the same mutation (substitution of T by C) was introduced into the regulatory region of the ydhL gene from B. amyloliquefaciens (position "-77" from start point of the gene) using QuickChange™ site-directed mutagenesis (Stratagene). For that purpose, two primers 1 and 2 (SEQ ID NO: 7 and 8, respectively) were designed based on the DNA sequence of the regulatory region of the ydhL gene from B. amyloliquefaciens. The DNA plasmid pYDHL2 (pMW118-ydhL$_{BA}$) was used as a template. The whole plasmid was amplified with the aforementioned primers and several plasmids containing the ydhL gene were obtained. These plasmids were sequenced using the primer 3 (SEQ ID NO: 9) and the presence of the desired T to C substitution was confirmed. The new pMW118-derivative plasmid containing the ydhL gene from B. amyloliquefaciens with the mutation in the regulatory region was marked as pYDHL5. The pYDHL5 plasmid linearized by cutting with EcoRI restrictase and ligated with pMX30 previously linearized with the same restrictase. Thus, a shuttle plasmid pYDHL6 containing the ydhL$_{Ba}$ gene having the mutation enhancing its expression level was obtained.

Example 9

Effect of Enhanced Expression of ydhL$_{Ba}$ Gene on Inosine Production by the B. amyloliquefaciens Inosine-Producing Strain.

The pYDHL6 plasmid and the pMWMX$_1$ shuttle vector each were transformed into B. subtilis 168 strain by a well-known method (Spizizen, J. Proc. Natl. Acad. Sci. USA, 44, 1072-1078 (1958)). The resulting strains, B. subtilis (pYDHL6) and B. subtilis (pMWMX$_1$), were used as donors in phage E40-mediated transduction to introduce pYDHL6 and pMWMX$_1$ plasmids into the strain B. subtilis G1136A (AJ1991, VKPM B-8994, ATCC19222) producing inosine and guanosine (U.S. Pat. No. 3,575,809). The strain B. subtilis G1136A has been re-identified by All-Russian National Collection of Industrial Microorganisms (VKPM) (Russia, 113545 Moscow, 1st Dorozhny proezd, 1) as Bacillus amyloliquefaciens and deposited under accession number (VKPM B-8994). Therefore, the strain thereafter will be designated as Bacillus amyloliquefaciens G1136A. Phage E40 is a PBS 1-like phage (Takanishi, R., J. Gen. Microbiol., 31, 211-217, (1963)) capable of propagating on B. subtilis and B. amyloliquefaciens cells. After the transduction the strains B. amyloliquefaciens G1136A (pMWMX1) and B. amyloliquefaciens G1136A (pYDHL6) were obtained.

These strains were each cultivated at 37° C. for 18 hours in L-broth with 10 mg/l erythromycin. Then 0.3 ml of the resulting culture was inoculated into 3 ml of a Bacillus fermentation medium containing 10 mg/l erythromycin, in a 20×200 mm test tube, and cultivated at 37° C. for 72 hours with a rotary shaker.

The composition of the fermentation medium: (g/l)

| | |
|---|---|
| Glucose | 80.0 |
| KH$_2$PO$_4$ | 1.0 |
| MgSO$_4$ | 0.4 |
| FeSO$_4$·7H$_2$O | 0.01 |
| MnSO$_4$·5H$_2$O | 0.01 |
| NH$_4$Cl | 15.0 |
| Adenine | 0.3 |
| Total nitrogen (in the form of Mameno) | 0.8 |
| CaCO$_3$ | 25.0 |

After the cultivation, the amount of inosine and guanosine that accumulated in the medium was determined by HPLC as above. The results are presented in Table 6.

TABLE 6

| Strain | OD$_{540}$ | Inosine, g/l |
|---|---|---|
| B. amyloliquefaciens G1136A (pMWMX1) | 16.7 | 1.8 ± 0.1 |
| B. amyloliquefaciens G1136A (pYDHL6) | 16.1 | 3.2 ± 0.1 |

As it is seen from the Table 6, the enhanced expression of the ydhL$_{Ba}$ gene due to the regulatory mutation improved inosine productivity of the B. amyloliquefaciens strain G1136A.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing a purine nucleotide comprising:
   (a) cultivating a bacterium belonging to the genus *Bacillus* in a culture medium to produce purine nucleoside,
   (b) phosphorylating the purine nucleoside to generate a purine nucleotide, and
   (c) collecting said purine nucleotide, wherein said bacterium has a purine nucleoside-producing ability and has been modified to have enhanced activity of a YdhL protein by a method selected from the group consisting of:
   (A) transforming the bacterium with a multi-copy vector containing a ydhL gene and/or introducing multiple copies of the ydhL gene into chromosome of the bacterium,
   (B) placing the ydhL gene under the control of a promoter capable of enhancing the expression of the ydhL gene, and
   (C) combinations thereof.

2. The method according to claim 1, wherein said purine nucleotide is 5'-inosinic acid.

3. The method according to claim 1, wherein said purine nucleotide is 5'-xanthylic acid.

4. The method according to claim 1, wherein said purine nucleotide is 5'-guanylic acid.

5. The method according to claim 1, wherein said bacterium has been further modified to have enhanced expression of a purine nucleoside biosynthesis gene by a method selected from the group consisting of:
   (i) transforming of the bacterium with a multi-copy vector containing the purine nucleoside biosynthesis gene and/or introducing multiple copies of the gene into chromosome of the bacterium,
   (ii) placing the purine nucleoside biosynthesis gene under the control of a promoter capable of enhancing the expression of the purine nucleoside biosynthesis gene, and
   (iii) combinations thereof.

6. A method for producing 5'-guanylic acid comprising
   (a) cultivating a bacterium belonging to the genus *Bacillus* in a culture medium to produce xanthosine,
   (b) phosphorylating xanthosine to generate 5'-xanthylic acid,
   (c) aminating 5'-xanthylic acid to generate 5'-guanylic acid, and
   (d) collecting 5'-guanylic acid,
wherein said bacterium has a purine nucleoside-producing ability and has been modified to have enhanced activity of a YdhL protein by a method selected from the group consisting of:
   (A) transforming the bacterium with a multi-copy vector containing a ydhL gene and/or introducing multiple copies of the ydhL gene into chromosome of the bacterium,
   (B) placing the ydhL gene under the control of a promoter capable of enhancing the expression of the ydhL gene, and
   (C) combinations thereof.

* * * * *

SEQUENCE LISTING

<160> NUMBER OF SEQ ID NOS: 9

<210> SEQ ID NO 1
<211> LENGTH: 1161
<212> TYPE: DNA
<213> ORGANISM: Bacillus amyloliquefaciens
<220> FEATURE:
<221> NAME/KEY: CDS
<222> LOCATION: (1)..(1161)

```
<400> SEQUENCE: 1 atg aat ttc aaa gta ttt ctg ctt gca gca tct act att gca gtc gga      48
Met Asn Phe Lys Val Phe Leu Leu Ala Ala Ser Thr Ile Ala Val Gly
1               5                   10                  15 ttg gtt gaa tta att gtg ggc ggt att ctc ccg caa atc gct tcc gac      96
Leu Val Glu Leu Ile Val Gly Gly Ile Leu Pro Gln Ile Ala Ser Asp
            20                  25                  30 tta gac ata tcg atc gtc agc gcc ggg cag ctg atc agc gtg ttc gcg     144
Leu Asp Ile Ser Ile Val Ser Ala Gly Gln Leu Ile Ser Val Phe Ala
        35                  40                  45 ctc ggt tac gcg gta tca ggc cct ctg ctt ttg gca gtg acg gca aaa     192
Leu Gly Tyr Ala Val Ser Gly Pro Leu Leu Leu Ala Val Thr Ala Lys
    50                  55                  60 gct gaa cga aag cgg ctt tat tta atc gca ctt ttt gtt ttc ttc ctg     240
Ala Glu Arg Lys Arg Leu Tyr Leu Ile Ala Leu Phe Val Phe Phe Leu
65                  70                  75                  80 agt aat ctg gtc gct tac ttc agt ccc aat ttc gcc gta ctt atg gtg     288
Ser Asn Leu Val Ala Tyr Phe Ser Pro Asn Phe Ala Val Leu Met Val
                85                  90                  95 tca cga gtg ctc gct tcc atg agc aca ggg ctg att gtc gtc ctt tct     336
Ser Arg Val Leu Ala Ser Met Ser Thr Gly Leu Ile Val Val Leu Ser
            100                 105                 110 tta acg att gct cct aaa atc gtg gcg ccg gaa tac aga gcg cgg gcg     384
Leu Thr Ile Ala Pro Lys Ile Val Ala Pro Glu Tyr Arg Ala Arg Ala
        115                 120                 125 atc ggc atc att ttc atg ggc ttc agc tcc gca atc gct tta ggc gtg     432
Ile Gly Ile Ile Phe Met Gly Phe Ser Ser Ala Ile Ala Leu Gly Val
    130                 135                 140 cct gtc ggc att atc atc agc aat gcc ttc gga tgg cgc gtg ctg ttt     480
Pro Val Gly Ile Ile Ile Ser Asn Ala Phe Gly Trp Arg Val Leu Phe
145                 150                 155                 160 ttg gga atc ggc gta tta tct ctg gtt tcc atg ctg att atc agc gtc     528
Leu Gly Ile Gly Val Leu Ser Leu Val Ser Met Leu Ile Ile Ser Val
                165                 170                 175 ttt ttt gaa aaa ata cct gct gaa aaa atg atc ccg ttc cgt gag cag     576
Phe Phe Glu Lys Ile Pro Ala Glu Lys Met Ile Pro Phe Arg Glu Gln
            180                 185                 190 att aaa acg att ggg aac gcc aag att gcc agc gcg cat ctt gtt acc     624
Ile Lys Thr Ile Gly Asn Ala Lys Ile Ala Ser Ala His Leu Val Thr
        195                 200                 205 tta ttt aca ttg gcg ggg cat tac aca cta tat gcc tac ttt gcg cct     672
Leu Phe Thr Leu Ala Gly His Tyr Thr Leu Tyr Ala Tyr Phe Ala Pro
    210                 215                 220 ttt ttg gaa aca acg ctt cat ttg agt tct gtt tgg gtc agt gta tgc     720
Phe Leu Glu Thr Thr Leu His Leu Ser Ser Val Trp Val Ser Val Cys
225                 230                 235                 240 tac ttt ttg ttc ggc ctg tca gcg gta tgc ggc ggc ccg ttc gga ggc     768
Tyr Phe Leu Phe Gly Leu Ser Ala Val Cys Gly Gly Pro Phe Gly Gly
                245                 250                 255 tgg ctg tat gac cgt tta gga tca ttt aaa agc atc atg ctt gtg acc     816
Trp Leu Tyr Asp Arg Leu Gly Ser Phe Lys Ser Ile Met Leu Val Thr
            260                 265                 270 gtt tct ttc gct ttg atc ctg ttt atc ctt ccg ctg tca acg gtt tct     864
Val Ser Phe Ala Leu Ile Leu Phe Ile Leu Pro Leu Ser Thr Val Ser
        275                 280                 285 tta atc gtt ttc ctg cct gcg atg gtc att tgg gga ttg ctc agc tgg     912
Leu Ile Val Phe Leu Pro Ala Met Val Ile Trp Gly Leu Leu Ser Trp
    290                 295                 300 agc ctt gcg ccg gcg cag caa agc tat ttg atc aaa atc gcg cct gag     960
```

```
Ser Leu Ala Pro Ala Gln Gln Ser Tyr Leu Ile Lys Ile Ala Pro Glu
305                 310                 315                 320 tct tcc gat att cag caa agc ttc aat acg tcc gct ttg caa atc ggc      1008
Ser Ser Asp Ile Gln Gln Ser Phe Asn Thr Ser Ala Leu Gln Ile Gly
                325                 330                 335 att gcg ctc ggg tca gcc atc ggc ggc ggc gtg atc gga caa acg ggt      1056
Ile Ala Leu Gly Ser Ala Ile Gly Gly Gly Val Ile Gly Gln Thr Gly
            340                 345                 350 tct gtc aca gca acc gcc tgg tgc ggc ggt ttg att gtc att atc gca      1104
Ser Val Thr Ala Thr Ala Trp Cys Gly Gly Leu Ile Val Ile Ile Ala
        355                 360                 365 gtc agc tta gcc gta ttc tct tta acg aga ccc gct ttg aaa aga aaa      1152
Val Ser Leu Ala Val Phe Ser Leu Thr Arg Pro Ala Leu Lys Arg Lys
370                 375                 380 tcc gca taa                                                           1161
Ser Ala
385

<210> SEQ ID NO 2
<211> LENGTH: 386
<212> TYPE: PRT
<213> ORGANISM: Bacillus amyloliquefaciens

<400> SEQUENCE: 2

Met Asn Phe Lys Val Phe Leu Leu Ala Ala Ser Thr Ile Ala Val Gly
1               5                   10                  15

Leu Val Glu Leu Ile Val Gly Gly Ile Leu Pro Gln Ile Ala Ser Asp
            20                  25                  30

Leu Asp Ile Ser Ile Val Ser Ala Gly Gln Leu Ile Ser Val Phe Ala
        35                  40                  45

Leu Gly Tyr Ala Val Ser Gly Pro Leu Leu Leu Ala Val Thr Ala Lys
    50                  55                  60

Ala Glu Arg Lys Arg Leu Tyr Leu Ile Ala Leu Phe Val Phe Phe Leu
65                  70                  75                  80

Ser Asn Leu Val Ala Tyr Phe Ser Pro Asn Phe Ala Val Leu Met Val
                85                  90                  95

Ser Arg Val Leu Ala Ser Met Ser Thr Gly Leu Ile Val Val Leu Ser
            100                 105                 110

Leu Thr Ile Ala Pro Lys Ile Val Ala Pro Glu Tyr Arg Ala Arg Ala
        115                 120                 125

Ile Gly Ile Ile Phe Met Gly Phe Ser Ser Ala Ile Ala Leu Gly Val
    130                 135                 140

Pro Val Gly Ile Ile Ile Ser Asn Ala Phe Gly Trp Arg Val Leu Phe
145                 150                 155                 160

Leu Gly Ile Gly Val Leu Ser Leu Val Ser Met Leu Ile Ile Ser Val
                165                 170                 175

Phe Phe Glu Lys Ile Pro Ala Glu Lys Met Ile Pro Phe Arg Glu Gln
            180                 185                 190

Ile Lys Thr Ile Gly Asn Ala Lys Ile Ala Ser Ala His Leu Val Thr
        195                 200                 205

Leu Phe Thr Leu Ala Gly His Tyr Thr Leu Tyr Ala Tyr Phe Ala Pro
    210                 215                 220

Phe Leu Glu Thr Thr Leu His Leu Ser Ser Val Trp Val Ser Val Cys
225                 230                 235                 240

Tyr Phe Leu Phe Gly Leu Ser Ala Val Cys Gly Gly Pro Phe Gly Gly
                245                 250                 255
```

```
Trp Leu Tyr Asp Arg Leu Gly Ser Phe Lys Ser Ile Met Leu Val Thr
            260                 265                 270

Val Ser Phe Ala Leu Ile Leu Phe Ile Leu Pro Leu Ser Thr Val Ser
        275                 280                 285

Leu Ile Val Phe Leu Pro Ala Met Val Ile Trp Gly Leu Leu Ser Trp
    290                 295                 300

Ser Leu Ala Pro Ala Gln Gln Ser Tyr Leu Ile Lys Ile Ala Pro Glu
305                 310                 315                 320

Ser Ser Asp Ile Gln Gln Ser Phe Asn Thr Ser Ala Leu Gln Ile Gly
                325                 330                 335

Ile Ala Leu Gly Ser Ala Ile Gly Gly Gly Val Ile Gly Gln Thr Gly
            340                 345                 350

Ser Val Thr Ala Thr Ala Trp Cys Gly Gly Leu Ile Val Ile Ile Ala
        355                 360                 365

Val Ser Leu Ala Val Phe Ser Leu Thr Arg Pro Ala Leu Lys Arg Lys
370                 375                 380

Ser Ala
385

<210> SEQ ID NO 3
<211> LENGTH: 1167
<212> TYPE: DNA
<213> ORGANISM: Bacillus subtilis
<220> FEATURE:
<221> NAME/KEY: CDS
<222> LOCATION: (1)..(1167)

<400> SEQUENCE: 3
```

| | | | | | | | | | | | | | | | | |
|---|---|---|---|---|---|---|---|---|---|---|---|---|---|---|---|---|
| atg | aat | ttc | aaa | gtt | ttc | ctg | ctt | gca | gct | tct | acg | att | gca | gtc | gga | 48 |
| Met | Asn | Phe | Lys | Val | Phe | Leu | Leu | Ala | Ala | Ser | Thr | Ile | Ala | Val | Gly | |
| 1 | | | 5 | | | | | 10 | | | | | 15 | | | |
| ttg | gtt | gag | tta | att | gtg | ggg | gga | att | ctt | cct | cag | atc | gca | aat | gat | 96 |
| Leu | Val | Glu | Leu | Ile | Val | Gly | Gly | Ile | Leu | Pro | Gln | Ile | Ala | Asn | Asp | |
| | | 20 | | | | | 25 | | | | | 30 | | | | |
| tta | gac | att | tcc | att | gtt | tca | gcc | gga | cag | ctg | atc | agt | gtg | ttt | gcg | 144 |
| Leu | Asp | Ile | Ser | Ile | Val | Ser | Ala | Gly | Gln | Leu | Ile | Ser | Val | Phe | Ala | |
| | 35 | | | | | 40 | | | | | 45 | | | | | |
| ctg | gga | tat | gca | gta | tct | ggg | ccg | ctg | ctt | ttg | gca | ttg | act | gcg | aag | 192 |
| Leu | Gly | Tyr | Ala | Val | Ser | Gly | Pro | Leu | Leu | Leu | Ala | Leu | Thr | Ala | Lys | |
| 50 | | | | | 55 | | | | | 60 | | | | | | |
| att | gag | cgg | aag | cgc | tta | tat | cta | att | gct | tta | ttt | gtt | ttc | ttc | ctt | 240 |
| Ile | Glu | Arg | Lys | Arg | Leu | Tyr | Leu | Ile | Ala | Leu | Phe | Val | Phe | Phe | Leu | |
| 65 | | | | 70 | | | | | 75 | | | | | 80 | | |
| agc | aat | ctt | gtc | gcc | tat | ttc | agc | cct | aat | ttc | gca | aca | ctg | atg | gta | 288 |
| Ser | Asn | Leu | Val | Ala | Tyr | Phe | Ser | Pro | Asn | Phe | Ala | Thr | Leu | Met | Val | |
| | | | | 85 | | | | | 90 | | | | | 95 | | |
| tct | agg | gta | ttg | gca | gca | atg | agt | aca | ggg | ctg | att | gtt | gtg | ctt | tct | 336 |
| Ser | Arg | Val | Leu | Ala | Ala | Met | Ser | Thr | Gly | Leu | Ile | Val | Val | Leu | Ser | |
| | | | | 100 | | | | | 105 | | | | | 110 | | |
| tta | aca | att | gcc | ccg | aaa | att | gta | gcg | cct | gaa | tac | aga | gcc | cgc | gca | 384 |
| Leu | Thr | Ile | Ala | Pro | Lys | Ile | Val | Ala | Pro | Glu | Tyr | Arg | Ala | Arg | Ala | |
| | | | 115 | | | | | 120 | | | | | 125 | | | |
| atc | gga | att | att | ttt | atg | gga | ttc | agc | tct | gct | atc | gca | tta | ggc | gtg | 432 |
| Ile | Gly | Ile | Ile | Phe | Met | Gly | Phe | Ser | Ser | Ala | Ile | Ala | Leu | Gly | Val | |
| | | | 130 | | | | | 135 | | | | | 140 | | | |
| ccg | ctc | gga | atc | tta | atc | agc | gat | tcc | ttc | ggg | tgg | cgg | att | ttg | ttc | 480 |
| Pro | Leu | Gly | Ile | Leu | Ile | Ser | Asp | Ser | Phe | Gly | Trp | Arg | Ile | Leu | Phe | |
| 145 | | | | | 150 | | | | | 155 | | | | | 160 | |
| ctt | ggc | atc | ggc | ctg | ttg | gca | ctg | atc | tcc | atg | ctg | att | att | tca | atc | 528 |

```
Leu Gly Ile Gly Leu Leu Ala Leu Ile Ser Met Leu Ile Ser Ile
            165                 170                 175 ttc ttt gaa aga ata ccg gcg gag aaa atg att cct ttc cgg gaa caa      576
Phe Phe Glu Arg Ile Pro Ala Glu Lys Met Ile Pro Phe Arg Glu Gln
            180                 185                 190 ctc aag acg atc ggt aat ctg aaa atc gcg agt tca cac ctc gtc acg      624
Leu Lys Thr Ile Gly Asn Leu Lys Ile Ala Ser Ser His Leu Val Thr
            195                 200                 205 atg ttt aca tta gct ggc cac tac acg ctt tac gct tac ttt gcg ccg      672
Met Phe Thr Leu Ala Gly His Tyr Thr Leu Tyr Ala Tyr Phe Ala Pro
    210                 215                 220 ttt tta gaa gag act ctt cac ctg agc tct ttc tgg gtc agc att tgt      720
Phe Leu Glu Glu Thr Leu His Leu Ser Ser Phe Trp Val Ser Ile Cys
225                 230                 235                 240 tat ttc ctt ttc ggg ata tct gct gta tgc gga ggc cct ttc gga gga      768
Tyr Phe Leu Phe Gly Ile Ser Ala Val Cys Gly Gly Pro Phe Gly Gly
                245                 250                 255 gcg cta tct gac cgg ctt ggt tcc ttt aag agc att ttg ctg gtg acc      816
Ala Leu Ser Asp Arg Leu Gly Ser Phe Lys Ser Ile Leu Leu Val Thr
                260                 265                 270 ggt tcc ttt gcc atc att atg ttc tta ctg ccg ctg tct aca tcg tct      864
Gly Ser Phe Ala Ile Ile Met Phe Leu Leu Pro Leu Ser Thr Ser Ser
            275                 280                 285 atg att ttc ttt ttg cct gtc atg gtg att tgg ggt ctt ctg agc tgg      912
Met Ile Phe Phe Leu Pro Val Met Val Ile Trp Gly Leu Leu Ser Trp
290                 295                 300 agc ctc gcc ccg gct cag caa agc tat tta att gaa att gca cct gat      960
Ser Leu Ala Pro Ala Gln Gln Ser Tyr Leu Ile Glu Ile Ala Pro Asp
305                 310                 315                 320 tcg tct gac att cag caa agc ttt aac aca tcg gcc ctc caa gtc gga     1008
Ser Ser Asp Ile Gln Gln Ser Phe Asn Thr Ser Ala Leu Gln Val Gly
                325                 330                 335 att gcc ctt ggc tca gcc att ggc ggt gtt gtt ttg gat cag acg ggt     1056
Ile Ala Leu Gly Ser Ala Ile Gly Gly Val Val Leu Asp Gln Thr Gly
                340                 345                 350 act gtg gtg tca acg gca tgg tgc ggc gga tcg att gtg atc atc gct     1104
Thr Val Val Ser Thr Ala Trp Cys Gly Gly Ser Ile Val Ile Ile Ala
            355                 360                 365 gtc ctg ttt gct ttc att tct tta aca aga cct gtt caa aca gca aaa     1152
Val Leu Phe Ala Phe Ile Ser Leu Thr Arg Pro Val Gln Thr Ala Lys
370                 375                 380 aaa tcc tcc ttg taa                                                 1167
Lys Ser Ser Leu
385

<210> SEQ ID NO 4
<211> LENGTH: 388
<212> TYPE: PRT
<213> ORGANISM: Bacillus subtilis

<400> SEQUENCE: 4

Met Asn Phe Lys Val Phe Leu Leu Ala Ala Ser Thr Ile Ala Val Gly
1               5                   10                  15

Leu Val Glu Leu Ile Val Gly Gly Ile Leu Pro Gln Ile Ala Asn Asp
                20                  25                  30

Leu Asp Ile Ser Ile Val Ser Ala Gly Gln Leu Ile Ser Val Phe Ala
            35                  40                  45

Leu Gly Tyr Ala Val Ser Gly Pro Leu Leu Leu Ala Leu Thr Ala Lys
    50                  55                  60
```

```
Ile Glu Arg Lys Arg Leu Tyr Leu Ile Ala Leu Phe Val Phe Phe Leu
 65                  70                  75                  80

Ser Asn Leu Val Ala Tyr Phe Ser Pro Asn Phe Ala Thr Leu Met Val
                 85                  90                  95

Ser Arg Val Leu Ala Ala Met Ser Thr Gly Leu Ile Val Val Leu Ser
            100                 105                 110

Leu Thr Ile Ala Pro Lys Ile Val Ala Pro Glu Tyr Arg Ala Arg Ala
        115                 120                 125

Ile Gly Ile Ile Phe Met Gly Phe Ser Ser Ala Ile Ala Leu Gly Val
    130                 135                 140

Pro Leu Gly Ile Leu Ile Ser Asp Ser Phe Gly Trp Arg Ile Leu Phe
145                 150                 155                 160

Leu Gly Ile Gly Leu Leu Ala Leu Ile Ser Met Leu Ile Ile Ser Ile
                165                 170                 175

Phe Phe Glu Arg Ile Pro Ala Glu Lys Met Ile Pro Phe Arg Glu Gln
            180                 185                 190

Leu Lys Thr Ile Gly Asn Leu Lys Ile Ala Ser Ser His Leu Val Thr
        195                 200                 205

Met Phe Thr Leu Ala Gly His Tyr Thr Leu Tyr Ala Tyr Phe Ala Pro
210                 215                 220

Phe Leu Glu Glu Thr Leu His Leu Ser Ser Phe Trp Val Ser Ile Cys
225                 230                 235                 240

Tyr Phe Leu Phe Gly Ile Ser Ala Val Cys Gly Gly Pro Phe Gly Gly
                245                 250                 255

Ala Leu Ser Asp Arg Leu Gly Ser Phe Lys Ser Ile Leu Leu Val Thr
            260                 265                 270

Gly Ser Phe Ala Ile Ile Met Phe Leu Leu Pro Leu Ser Thr Ser Ser
        275                 280                 285

Met Ile Phe Phe Leu Pro Val Met Val Ile Trp Gly Leu Leu Ser Trp
290                 295                 300

Ser Leu Ala Pro Ala Gln Gln Ser Tyr Leu Ile Glu Ile Ala Pro Asp
305                 310                 315                 320

Ser Ser Asp Ile Gln Gln Ser Phe Asn Thr Ser Ala Leu Gln Val Gly
                325                 330                 335

Ile Ala Leu Gly Ser Ala Ile Gly Gly Val Val Leu Asp Gln Thr Gly
            340                 345                 350

Thr Val Val Ser Thr Ala Trp Cys Gly Gly Ser Ile Val Ile Ile Ala
        355                 360                 365

Val Leu Phe Ala Phe Ile Ser Leu Thr Arg Pro Val Gln Thr Ala Lys
    370                 375                 380

Lys Ser Ser Leu
385

<210> SEQ ID NO 5
<211> LENGTH: 31
<212> TYPE: DNA
<213> ORGANISM: Artificial sequence
<220> FEATURE:
<223> OTHER INFORMATION: primer

<400> SEQUENCE: 5
cccgtcgaca aaacggcatc cgcttttctc a                                    31

<210> SEQ ID NO 6
<211> LENGTH: 32
<212> TYPE: DNA
```

```
<213> ORGANISM: Artificial sequence
<220> FEATURE:
<223> OTHER INFORMATION: primer

<400> SEQUENCE: 6
cccagatctc gagcggcgaa aaagtgaaaa ac                              32

<210> SEQ ID NO 7
<211> LENGTH: 34
<212> TYPE: DNA
<213> ORGANISM: Artificial sequence
<220> FEATURE:
<223> OTHER INFORMATION: primer

<400> SEQUENCE: 7
gaaccgtaaa atcctgacta caaaaaactg tccc                            34

<210> SEQ ID NO 8
<211> LENGTH: 34
<212> TYPE: DNA
<213> ORGANISM: Artificial sequence
<220> FEATURE:
<223> OTHER INFORMATION: primer

<400> SEQUENCE: 8
gggacagttt tttgtagtca ggattttacg gttc                            34

<210> SEQ ID NO 9
<211> LENGTH: 23
<212> TYPE: DNA
<213> ORGANISM: Artificial sequence
<220> FEATURE:
<223> OTHER INFORMATION: primer

<400> SEQUENCE: 9
atttgcggga gaataccgcc cac                                        23
```